US010285665B2

United States Patent
Lee et al.

(10) Patent No.: US 10,285,665 B2
(45) Date of Patent: May 14, 2019

(54) ULTRASOUND DIAGNOSIS APPARATUS AND METHOD AND COMPUTER-READABLE STORAGE MEDIUM

(71) Applicant: SAMSUNG MEDISON CO., LTD., Hongcheon-gun (KR)

(72) Inventors: Seung-ju Lee, Hongcheon-gun (KR); Ji-woo Kim, Hongcheon-gun (KR); Yoon-woo Jun, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 531 days.

(21) Appl. No.: 14/739,138

(22) Filed: Jun. 15, 2015

(65) Prior Publication Data

US 2016/0113626 A1 Apr. 28, 2016

(30) Foreign Application Priority Data

Oct. 27, 2014 (KR) ........................ 10-2014-0146426

(51) Int. Cl.
*A61B 8/00* (2006.01)
*A61B 5/00* (2006.01)

(52) U.S. Cl.
CPC ............ *A61B 8/464* (2013.01); *A61B 5/0035* (2013.01); *A61B 8/463* (2013.01); *A61B 8/469* (2013.01); *A61B 5/0095* (2013.01); *A61B 5/748* (2013.01); *A61B 5/7445* (2013.01); *A61B 8/465* (2013.01); *A61B 8/467* (2013.01)

(58) Field of Classification Search
CPC .................................................... A61B 8/464
See application file for complete search history.

(56) References Cited

U.S. PATENT DOCUMENTS

| | | |
|---|---|---|
| 5,954,650 A | 9/1999 | Saito et al. |
| 6,520,912 B1 | 2/2003 | Brooks et al. |
| 8,416,346 B2 | 4/2013 | Bae et al. |
| 8,606,045 B2 | 12/2013 | Lee |
| 2008/0063305 A1 | 3/2008 | Lim |

(Continued)

FOREIGN PATENT DOCUMENTS

| | | |
|---|---|---|
| EP | 2759951 A2 | 7/2014 |
| KR | 10-2010-0036664 A | 4/2010 |

(Continued)

OTHER PUBLICATIONS

Communication dated Mar. 31, 2016, from the European Patent Office in counterpart European Application No. 15166619.5.

*Primary Examiner* — Rochelle D Turchen
(74) *Attorney, Agent, or Firm* — Sughrue Mion, PLLC

(57) ABSTRACT

Provided are an ultrasound diagnosis apparatus and a method of operating the ultrasound diagnosis apparatus that are capable of efficiently controlling screens of a plurality of displays. The ultrasound diagnosis apparatus includes: a first display configured to display first images in a first image layout; a second display configured to display second images in a second image layout; a user input unit configured to receive an input for selecting at least one from among the first images; and a controller configured to control displaying of at least one selected from the second images and the at least one selected image on the second display in a third image layout.

23 Claims, 17 Drawing Sheets

(56) References Cited

U.S. PATENT DOCUMENTS

| | | | |
|---|---|---|---|
| 2009/0080719 A1* | 3/2009 | Watt | G06F 3/1446 |
| | | | 382/128 |
| 2010/0125196 A1 | 5/2010 | Park et al. | |
| 2013/0197364 A1 | 8/2013 | Han | |
| 2013/0335348 A1 | 12/2013 | Nam et al. | |
| 2014/0081140 A1 | 3/2014 | Kim et al. | |
| 2014/0121524 A1 | 5/2014 | Chiang et al. | |
| 2015/0209013 A1* | 7/2015 | Tsymbalenko | A61B 8/485 |
| | | | 600/440 |

FOREIGN PATENT DOCUMENTS

| | | |
|---|---|---|
| KR | 10-1132536 B1 | 4/2012 |
| KR | 10-1365242 B1 | 2/2014 |

\* cited by examiner

ULTRASOUND DIAGNOSIS APPARATUS AND METHOD AND COMPUTER-READABLE STORAGE MEDIUM

RELATED APPLICATION

This application claims the benefit of Korean Patent Application No. 10-2014-0146426, filed on Oct. 27, 2014, in the Korean Intellectual Property Office, the disclosure of which is incorporated herein in its entirety by reference.

BACKGROUND

1. Field

One or more exemplary embodiments relate to an ultrasound diagnosis apparatus and method and a computer-readable storage medium, and more particularly, to an ultrasound diagnosis apparatus and method adapted to facilitate observation of an object during ultrasound diagnosis.

2. Description of the Related Art

An ultrasound diagnosis apparatus transmits ultrasound signals generated by transducers located in a probe to an object and receives echo signals reflected from the object, thereby obtaining images of an inner area of the object. In particular, an ultrasound diagnosis apparatus may be used for medical purposes such as observing an inner area of an object, detecting foreign substances, and assessing injuries. The ultrasound diagnosis apparatus may have stable imaging performance and display information regarding an object in real-time compared to an X-ray diagnosis apparatus. Furthermore, unlike an X-ray diagnosis apparatus, there is no risk of radiation exposure when an ultrasound diagnosis apparatus is used, and thus, the ultrasound diagnosis apparatus is very safe. Therefore, an ultrasound diagnosis apparatus is widely used together with other types of imaging diagnosis devices.

In recent years, as displays have become less expensive, ultrasound diagnosis apparatuses equipped with a plurality of large screen, high-resolution displays have been increasingly used. However, even when an ultrasound diagnosis apparatus has two or more displays, the ultrasound diagnosis apparatus may provide the same image or an image designated for each display to the two or more displays.

Thus, there is a need for an ultrasound diagnosis apparatus and a method of operating the ultrasound diagnosis apparatus which are capable of efficiently controlling screens of a plurality of displays.

SUMMARY

One or more exemplary embodiments include an ultrasound diagnosis apparatus and a method of operating the ultrasound diagnosis apparatus, which are capable of efficiently controlling screens of a plurality of displays.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a first display configured to display first images in a first image layout; a second display configured to display second images in a second image layout; a user input unit configured to receive an input for selecting at least one from among the first images; and a controller configured to control displaying of at least one selected from the second images and the at least one selected image on the second display in a third image layout.

The controller may control displaying of the remaining ones of the first images other than the at least one selected image on the first display in a fourth image layout.

The controller may set the fourth image layout so that an entire screen of the first display is filled with the remaining ones of the first images.

In the first image layout, the first images may be superimposed on one another.

The first images may include at least one selected from a Doppler image, a color Doppler image, an elasticity image, a photoacoustic image, an image using contrast medium, and a fusion image.

The controller may set the third image layout so that at least some of the second images and the at least one selected image are superimposed on one another.

The controller may set the third image layout so that at least some of the second images and the at least one selected image are not superimposed on one another.

The controller may set the third image layout so that an entire screen of the second display is filled with the second images and the at least one selected image.

The at least one selected image may be an image of a region of interest (ROI) selected by a user from at least one of the first images.

The first images may be thumbnail images, and the at least one selected image may be at least one of the thumbnail images.

The user input unit may receive a predetermined input, and the controller may control at least one of a size and a position of at least one image included in the first and second images based on the predetermined input.

The input for selecting at least one from among the first images may include at least one selected from a touch input, a touch gesture input, and a button input.

The first and second images may each include at least one selected from magnetic resonance imaging (MRI), computed tomography (CT), and ultrasound images.

According to one or more exemplary embodiments, a method of operating an ultrasound diagnosis apparatus includes: displaying first images on a first display in a first image layout; displaying second images on a second display in a second image layout; receiving an input for selecting at least one from among the first images; and controlling displaying of at least one selected from the second images and the at least one selected image on the second display in a third image layout.

The method may further include displaying the remaining ones of the first images other than the at least one selected image on the first display in a fourth image layout.

The method may further include setting the fourth image layout so that an entire screen of the first display is filled with the remaining ones of the first images.

In the first image layout, the first images may be superimposed on one another.

The first images may include at least one selected from a Doppler image, a color Doppler image, an elasticity image, a photoacoustic image, an image using contrast medium, and a fusion image.

The method may further include setting the third image layout so that at least some of the second images and the at least one selected image are not superimposed on one another.

The method may further include setting the third image layout so that an entire screen of the second display is filled with the second images and the at least one selected image.

The at least one selected image may be an image of an ROI selected by a user from at least one of the first images.

The first images may be thumbnail images, and the at least one selected image may be at least one of the thumbnail images.

The method may further include receiving a predetermined input and controlling at least one of a size and a position of at least one image included in the first and second images based on the predetermined input.

The input for selecting at least one from among the first images may include at least one selected from a touch input, a touch gesture input, and a button input.

The first and second images may each include at least one selected from MRI, CT, and ultrasound images.

According to one or more exemplary embodiments, a non-transitory computer-readable recording medium has recorded thereon a program for executing the method of operating an ultrasound diagnosis apparatus on a computer.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
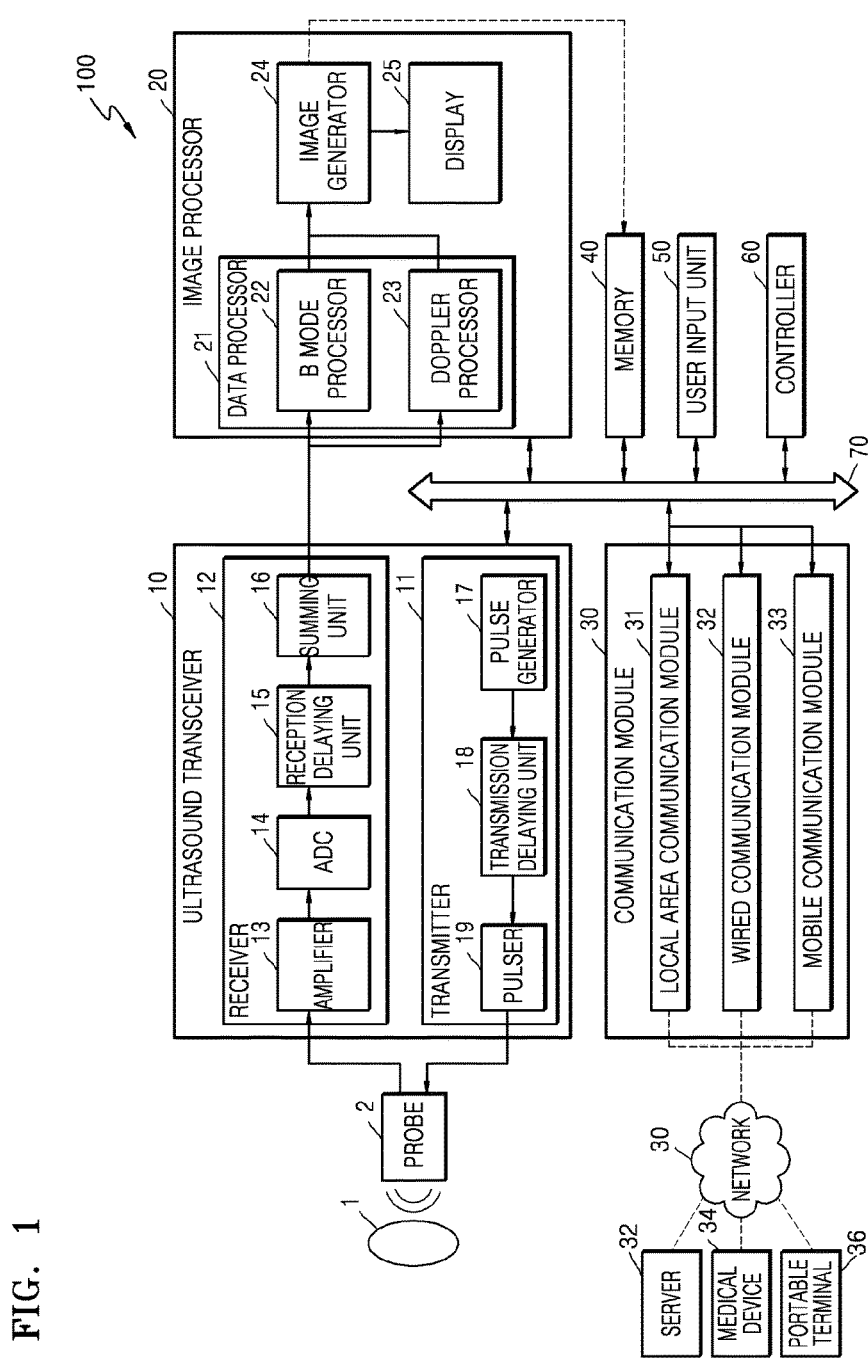
FIG. 1 is a block diagram of a configuration of an ultrasound diagnosis apparatus according to exemplary embodiments.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms used in this specification are those general terms currently widely used in the art in consideration of functions regarding the present invention, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as ". . . unit", ". . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Embodiments now will be described more fully hereinafter with reference to the accompanying drawings, in which illustrative embodiments are shown.

FIG. 1 is a diagram illustrating an ultrasound imaging apparatus 100 according to exemplary embodiments.

FIG. 1 illustrates an overall configuration of the ultrasound diagnosis apparatus 100 according to exemplary embodiments.

Referring to FIG. 1, the ultrasound diagnosis apparatus 100 may include a probe 2, an ultrasound transceiver 10, an image processor 20, a communication module 30, a display 300, a memory 40, a user input unit 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly.

A transmitter 11 supplies a driving signal to the probe 2. The transmitter 1110 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 120 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 1124 by delay times necessary for determining reception directionality, and the summing unit 16 generates ultrasound data by summing the echo signals processed by the reception delaying unit 15. Also, according to embodiments of the present invention, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components.

Similarly, a Doppler processor 23 may extract Doppler components from ultrasound data, and the image generator 24 may generate a Doppler image indicating a movement of an object as colors or waveforms based on the extracted Doppler components.

According to an embodiment of the present invention, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments of the present invention.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

the local area communication module 31 refers to a module for local area communication within a predetermined distance. Examples of local area communication techniques according to an embodiment of the present invention may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment of the present invention may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The user input unit 50 refers to a means via which a user inputs data for controlling the ultrasound diagnosis apparatus 100. The user input unit 50 may include hardware components, such as a keypad, a mouse, a touch panel, a touch screen, and a jog switch. However, embodiments of the present invention are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the user input unit 50 shown in FIG. 1.

All or some of the probe 2, the ultrasound transceiver 10, the image processor 20, the communication module 30, the memory 40, the user input unit 50, and the controller 60 may be implemented as software modules. However, embodiments of the present invention are not limited thereto, and some of the components stated above may be implemented as hardware modules. Furthermore, at least one selected from the ultrasound transceiver 10, the image processor 20, and the communication module 30 may be included in the controller 1700. However, embodiments of the present invention are not limited thereto.

A marker may be set to indicate a predetermined position or set a diagnosis region in an ultrasound image including an object.

In detail, the marker may be set at a portion that is to be observed in detail by the user to diagnose a disease or to check the health of a patient. The inventive concept provides an ultrasound diagnosis apparatus and an ultrasound image display method, which may change and output an ultrasound image to more accurately diagnose an object region in which the marker is set.

Figure 2:
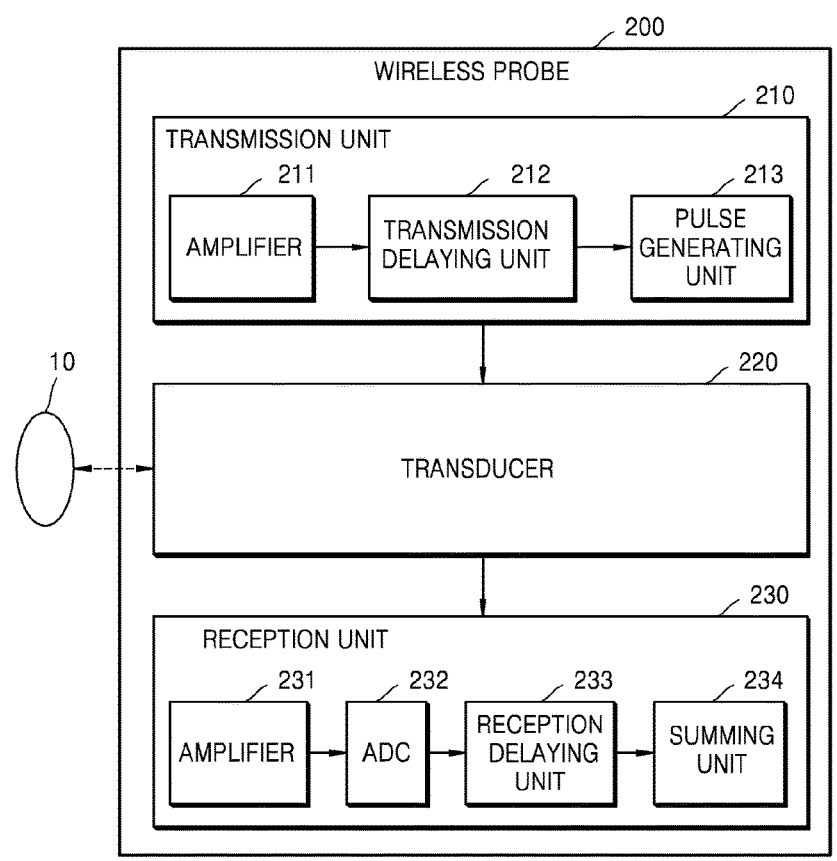
FIG. 2 is a block diagram of a configuration of a wireless probe according to an exemplary embodiment.

FIG. 2 is a block diagram showing a configuration of a wireless probe 200 according to an embodiment of the present invention.

As described above with reference to FIG. 1, the wireless probe 200 may include a plurality of transducers, and, according to embodiments of the present invention, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments of the present invention, the wireless probe 200 may selectively include a reception delaying unit 233 and a summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

In recent years, as displays have become less expensive, ultrasound diagnosis apparatuses equipped with a plurality of large screen, high-resolution displays have been increasingly used. However, even when an ultrasound diagnosis apparatus has two or more displays, the ultrasound diagnosis apparatus may provide the same image or an image designated for each display to the two or more displays.

Thus, there is a need for an ultrasound diagnosis apparatus and a method of operating the ultrasound diagnosis apparatus which are capable of efficiently controlling screens of a plurality of displays.

Hereinafter, an ultrasound diagnosis apparatus and method of operating the ultrasound diagnosis apparatus which are capable of efficiently controlling images on a plurality of displays and a computer-readable storage medium according to exemplary embodiments will be described in detail with reference to FIGS. 3 through 14.

Figure 3:
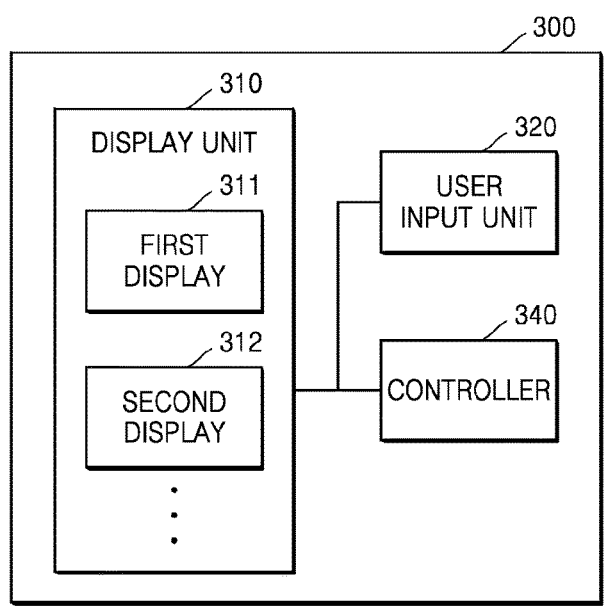
FIG. 3 is a block diagram of a configuration of an ultrasound diagnosis apparatus according to an exemplary embodiment.

FIG. 3 is a block diagram of a configuration of an ultrasound diagnosis apparatus 300 according to an exemplary embodiment.

The ultrasound diagnosis apparatus 300 according to the present embodiment includes all electronic devices capable of receiving, processing and/or outputting an ultrasound image. Furthermore, the ultrasound diagnosis apparatus 300 may receive, process, and/or output medical images generated by external ultrasound imaging devices, CT devices, or MRI devices.

The ultrasound diagnosis apparatus 300 according to the present embodiment may include a display unit 310, a user input unit 320, and a controller 340. The display unit 310 includes a plurality of displays, e.g., first and second displays 311 and 312. The display unit 310, the user input unit 320, and the controller 340 may correspond to their counterparts in FIG. 1, i.e., the display 25, the user input unit 50, and the controller 60, respectively.

The first display 311 may display first images in a first image layout. The second display 312 may display second images in a second image layout. The user input unit 320 may receive an input for selecting at least one from among the first images. Furthermore, the controller 340 may control displaying of at least one selected from the second images and the at least one selected first image on the second display 312 in a third image layout.

The first and second images each include a plurality of independent medical images. For example, the first and second images may each include at least one selected from MRI, CT, and ultrasound images. The ultrasound diagnosis apparatus 300 may acquire an ultrasound image from the image generator 24 of FIG. 1 as well as from external device. For example, the ultrasound diagnosis apparatus 300 may acquire at least one selected from MRI, CT, and ultrasound images from the server (35 of FIG. 1), the medical apparatus (34 of FIG. 1), and the portable terminal (36 of FIG. 1) via the network (3 of FIG. 1). The ultrasound diagnosis apparatus 300 may display images acquired from various types of devices on the display unit 310 to thereby allow a user to easily compare and analyze the images.

An image layout refers to a configuration in which a plurality of images are arranged on a single screen. The image layout will now be described in detail with reference to FIG. 4.

Figure 4A:
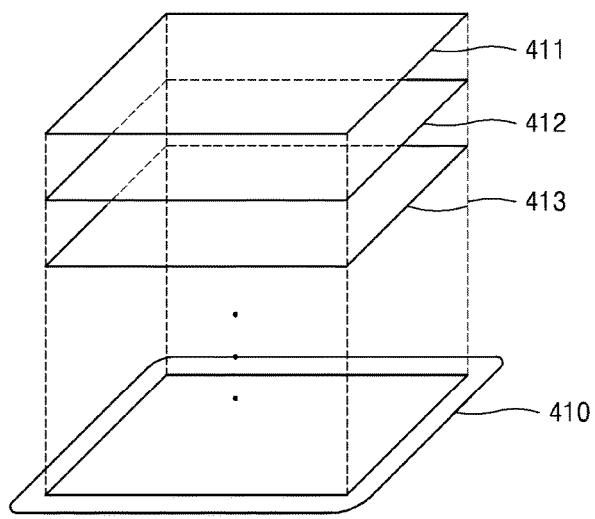
FIGS. 4A and 4B illustrate various image layouts according to an exemplary embodiment.
Figure 4B:
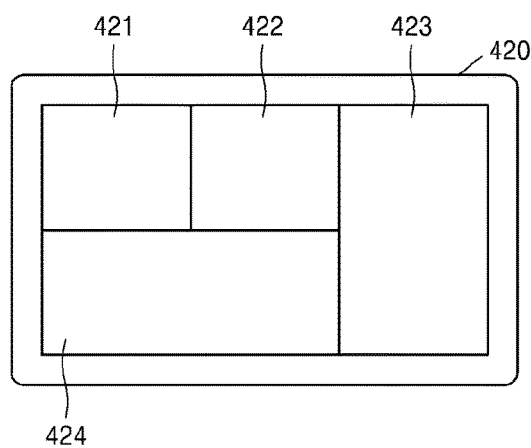

FIGS. 4A and 4B illustrate various image layouts according to an exemplary embodiment.

FIG. 4A illustrates an image layout in which a plurality of images 411 through 413 are arranged on a display 410 so that they overlap one another. The plurality of images 411 through 413 may be first images arranged on a first display or second images arranged on a second display.

Referring to FIG. 4A, the plurality of images 411 through 413 overlap one another entirely. However, the plurality of images 411 through 413 may overlap one another only partially. For example, the image 411 may overlap only a portion of the image 412. The ultrasound diagnosis apparatus 300 may determine whether the images 411 and 412 overlap each other only partially based on a user's selection. The display 410 may display at least a portion of at least one of the plurality of images 411 through 413 transparently. Since the display 410 displays at least a portion of the image 411 transparently, the display 410 may display the image 412 arranged behind the image 411 so that the image 412 is visible. If the display 410 displays the image 411 opaquely, the display 410 fails to display the image 412_so the image 412 is invisible on the display 410).

FIG. 4B illustrates an image layout in which a plurality of images 421 through 424 are arranged on a display 420 so that they do not overlap one another. The plurality of images 411 through 413 may be arranged on their unique regions so that they do not overlap one another.

FIG. 4A shows that all of the plurality of images 412 through 414 overlap one another, and FIG. 4B illustrates that the plurality of images 421 through 424 do not overlap one another. However, exemplary embodiments are not limited thereto, but overlapping and non-overlapping images may be displayed together on a single display. For example, the display 420 may display the images 421 and 422 in an overlapping manner while simultaneously displaying the images 422 and 423 in a non-overlapping manner. First and second images to be described below may be arranged in at least one of the image layouts illustrated in FIGS. 4A and 4B.

Figure 5A:
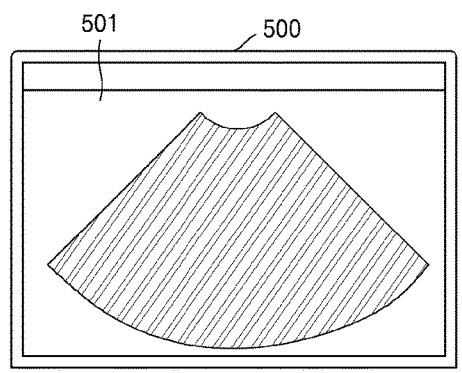
FIGS. 5A and 5B illustrates examples of images displayed by an ultrasound diagnosis apparatus according to an exemplary embodiment.
Figure 5B:
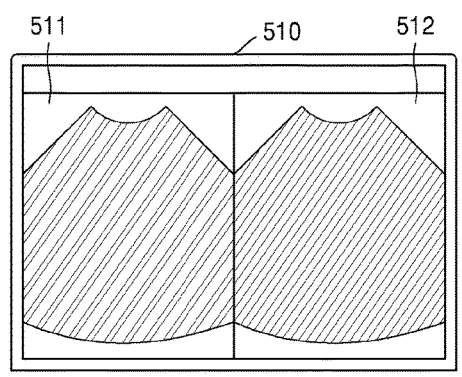

FIGS. 5A through 5B illustrate an example of images displayed by an ultrasound diagnosis apparatus.

Referring to FIG. 5A, a display 500 may display a single image 501 on the entire screen so that a user can easily view the entire image 501 on the single display 500. Furthermore, referring to FIG. 5B, a single display 510 may display a plurality of images 511 and 512. In this case, the display 510 may not display a portion of each of the plurality of images 511 and 512. For example, the display 510 may display an image 511 that is a portion of the image 501. Thus, it may be difficult for a user to view the images 511 and 512 in their entireties on the display 510.

The display 510 may reduce the images 511 and 512 based on the user's selection so that the user may observe reduced versions of the images 511 and 512 via the display 510. However, since the reduced versions of the images 511 and 512 have smaller sizes, the user cannot observe the images 511 and 512 minutely.

Exemplary embodiments will now be described in detail with reference to FIGS. 6 through 13. It is hereinafter assumed that an ultrasound diagnosis apparatus according to an exemplary embodiment has the same configuration as the ultrasound diagnosis apparatus 300 of FIG. 3.

Figure 6A:
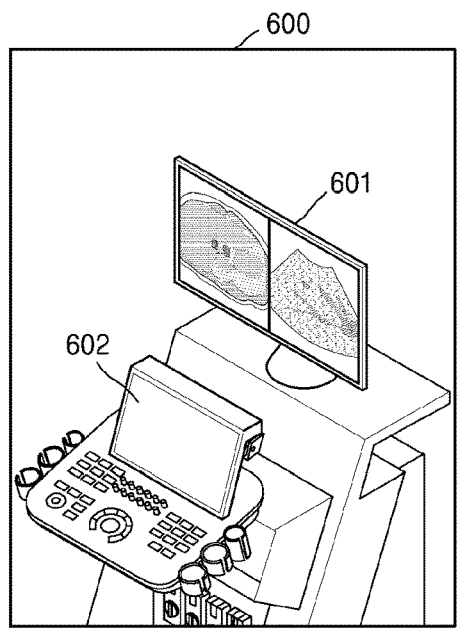
FIGS. 6A through 6C illustrate an implementation of an ultrasound diagnosis apparatus according to an exemplary embodiment.
Figure 6B:
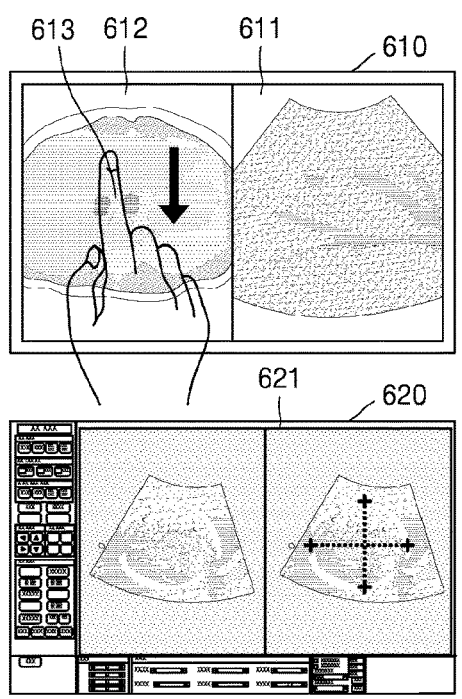
Figure 6C:
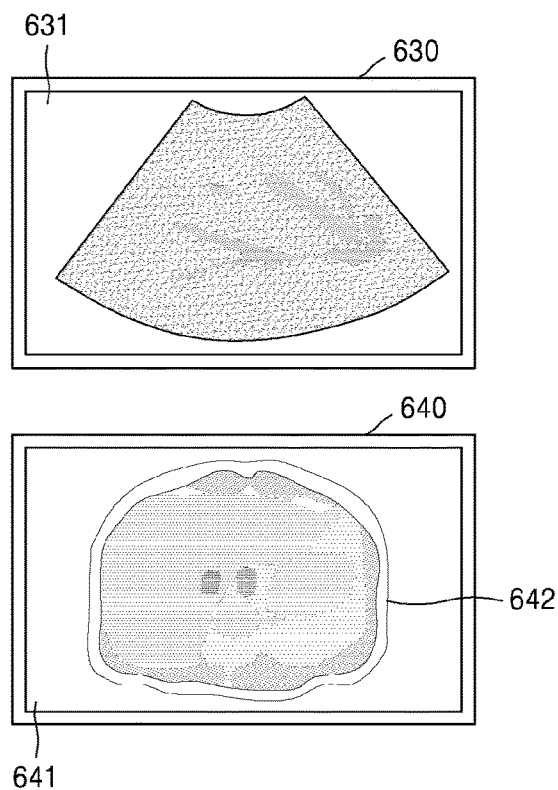

FIGS. 6A through 6C illustrate an implementation of an ultrasound diagnosis apparatus 600 according to an exemplary embodiment. Referring to FIG. 6A, the ultrasound diagnosis apparatus 600 may include a plurality of displays, e.g., first and second displays 601 and 602. The first and second displays 601 and 602 may correspond to the first and second displays 311 and 312 shown in FIG. 3, respectively.

Referring to FIG. 6B, the first display 610 may include at least one image, e.g., first images including images 611 and 612. The first display 610 may display the images 611 and 612 in a non-overlapping manner. The first images may include at least one selected from ultrasound, MRI, and CT images.

Furthermore, the second display 620 may display second images including an image 621. For example, the second images may include at least one selected from ultrasound, MRI, and CT images. Furthermore, the second display 620 may display menus for controlling the ultrasound diagnosis apparatus 600. The menus may include a probe parameter setting menu, a menu related to processing of an ultrasound image, etc. For convenience of explanation, FIG. 6B shows only the image 621 indicating a menu for controlling the ultrasound diagnosis apparatus 600.

The user input unit (320 of FIG. 3) may receive an input for selecting the image 612 from among the first images. An input for selecting at least one from among a plurality of images may include at least one selected from a touch input, a touch gesture input, and a button input. For example, the user input unit 320 may receive an input that occurs when a user taps the image 612 and drags it towards the second display 620, but exemplary embodiments are not limited thereto.

FIG. 6C illustrates first and second displays 630 and 640 after the user input unit 320 receives an input for selecting an image.

Referring to FIG. 6C, the controller (340 of FIG. 3) may control displaying of the image 612 selected from among the first images as shown in FIG. 6B on the second display 640 in a third image layout. For example, the second display 640 may display only an image 641. In other words, the second display 640 may display the image 641 including the whole image 642 of an object, which is different from the image 612 shown in FIG. 6B. Thus, the user may compare the image 641 with an image 631 more easily.

Alternatively, in the third image layout, the image 611 selected from among the first images may be arranged in front of all of the second images so that the image 611 is superimposed onto the second images. For example, the selected image 611 may correspond to the image 411 shown in FIG. 4, and the second images may correspond to the image 412 shown in FIG. 4. Since the image 611 shown in FIG. 6B is not transparent, the second display 640 may not display the image 621 overlapped by the image 611 so the image 621 is invisible. Thus, the second display 640 may display only the image 641 obtained by displaying the image 612 shown in FIG. 6B on a wide screen.

The second display 640 may also reduce the image 641 based on an input received via the user input unit 320. The controller 340 may move the image 641 towards the first display 630 based on an input received via the user input unit 320. In this case, the second display 640 may display the image 621 again.

The controller 340 may also control displaying of the remaining ones of the first images other than a selected image on the first display 630 in a fourth image layout. The controller 340 may set the fourth image layout so that the entire screen of the first display 630 is filled with the remaining first images other than the selected image 611. For example, the first display 630 may display the image 612 shown in FIG. 6B on the entire screen, i.e., the image 631, thereby allowing the user to more easily observe the image 631 on a large screen.

Figure 7A:
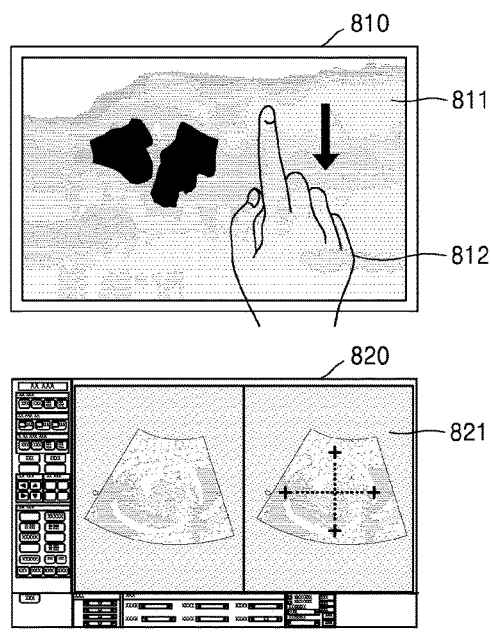
FIGS. 7A and 7B are diagrams of first and second displays of an ultrasound diagnostic apparatus according to an exemplary embodiment.
Figure 7B:
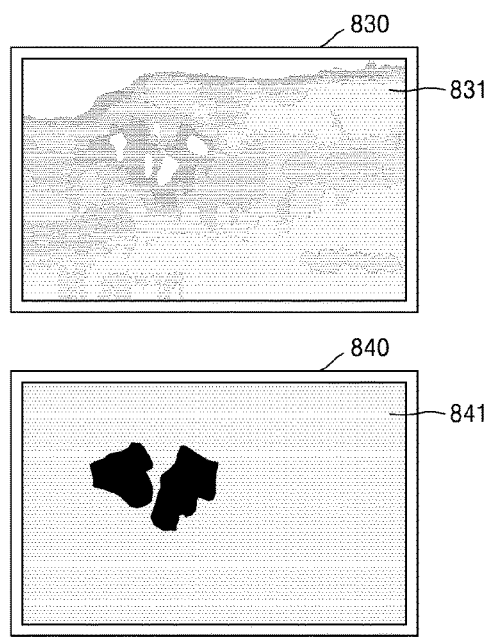

FIGS. 7A and 7B illustrate first displays 810 and 830 and second displays 820 and 840 of the ultrasound diagnosis apparatus (300 of FIG. 3) according to an exemplary embodiment.

Referring to FIG. 7A, the ultrasound diagnosis apparatus 300 may include the first and second displays 810 and 820. The first display 810 may display first images 811 in a first image layout. For example, in the first image layout, as described above with reference to FIG. 4A, at least some of the first images 811 may be superimposed over one another. Furthermore, the first images 811 may include at least one selected from a Doppler image, a color Doppler image, an elasticity image, a photoacoustic image, an image using contrast medium, and a fusion image. The second display 820 may display second images 821 in a second image layout.

The Doppler image is an image depicted by employing a change in frequency of a reflected sound wave due to the Doppler effect to determine whether an object is moving towards or away from a probe. The color Doppler image represents information about whether an object is moving towards or away from a probe as colors. The elasticity image represents elasticity of soft tissue. The photoacoustic image is a high-resolution image generated using a laser. The contrast image shows the object more clearly by injecting a contrast medium into the object. The fusion image may be produced by displaying MRI, CT, and ultrasound images together.

The user input unit 320 may receive an input for selecting at least one from among the first images 811. For example, the user input unit 320 may receive an input when a user 812 taps one of the first images 811 and drags it towards the second display 820. The selected image may be displayed at the foremost among the superimposed first images 811.

Referring to FIG. 7B, the controller 340 may control displaying of the remaining ones of the first images 811 other than the selected image on the first display 830 in a fourth image layout. The controller 340 may also control displaying of at least one selected from the second images 821 and an image 841 corresponding to the selected image on the second display 840 in a third image layout. For example, the second display 840 may display only the image 841.

Furthermore, according to another exemplary embodiment, the first display 830 may display the first images 811. In detail, the first display 830 may continuously display the first images 811, and the second display 840 may display a plurality of layers in the first images 811 one by one based on an input received from the user 812 via the user input unit 320. Furthermore, the second display 840 may display at least two of the plurality of layers in the first images 811 in an overlapping manner. Thus, the user is able to more easily observe an image corresponding to each layer in the first images 811 on the second display 840.

Furthermore, the first images 811 displayed on the first display 830 may be independent of the selected image 841. For example, the first display 830 may display the first images 811 instead of the image 831. Furthermore, the second display 840 may display the image 841 selected by the user based on the user's selection. The first images 811 may be moving images that change over time. The image 841 displayed on the second display 840 may be a still image from among the first images 811, which was at a time point selected by the user 812. Thus, the user 812 is able to more easily observe an image captured at a specific time point on the second display 840.

Figure 8A:
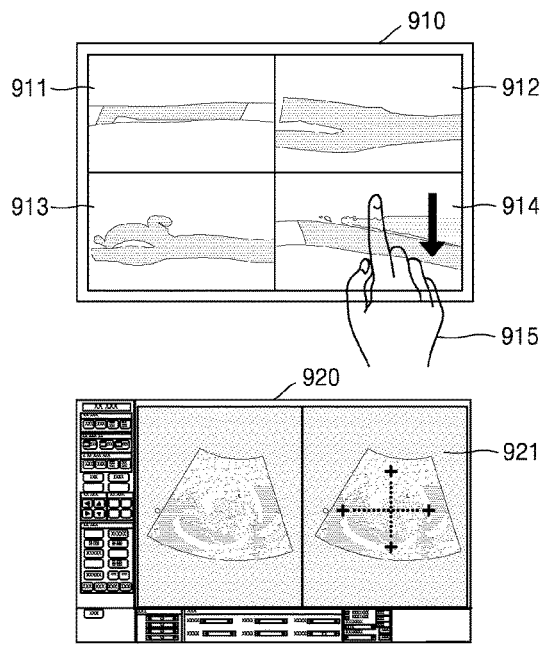
FIGS. 8A and 8B are diagrams of first and second displays of an ultrasound diagnosis apparatus according to an exemplary embodiment.
Figure 8B:
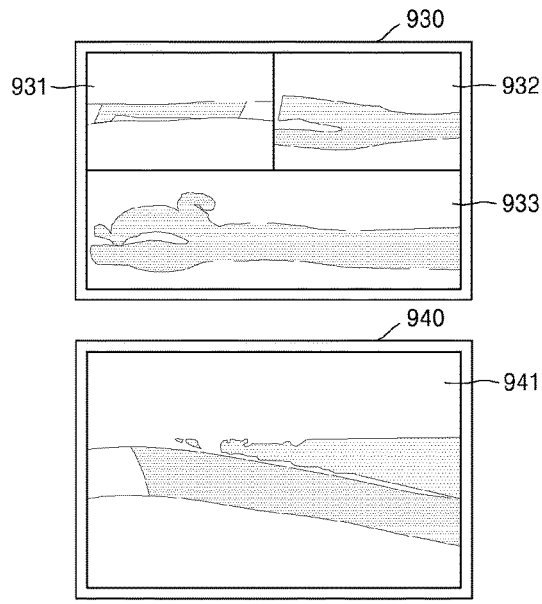

FIGS. 8A and 8B are diagrams of first displays 910 and 930 and second displays 920 and 940 of the ultrasound diagnosis apparatus 300 according to another exemplary embodiment.

Referring to FIG. 8A, the ultrasound diagnosis apparatus 300 may include the first and second displays 910 and 920. The first display 10 may display first images 911 through 914 in a first image layout. For example, in the first image layout, the first images 911 through 914 may be arranged so that they are superimposed over one another. The second display 920 may display second images 921 in a second image layout.

The user input unit 320 may receive an input for selecting at least one from among the first images 911 through 914 from a user 915. For example, the user input unit 320 may receive an input when the user 915 taps the first image 914 and drags it towards the second display 920.

Referring to FIG. 8B, according to an exemplary embodiment, the controller 340 may control images 931 through 933 corresponding to the remaining first images 911 through 913 other than the selected image 914 on the first display 930 in a fourth image layout. For example, the controller 340 may set the fourth image layout so that the entire screen of the first display 930 is filled with the images 931 through 933. In other words, at least one of the images 931 through 933 may be enlarged so as to fill a space where the image 914 was previously displayed. For example, as shown in FIG. 8B, the image 933 may be enlarged.

The controller 340 may also control displaying of at least one selected from the second images 921 and an image 941 corresponding to the selected image 914 on the second display 940 in a third image layout. In the third image layout, the image 941 may be displayed in front of the second images 921 so that they are superimposed on one another. Thus, the second display 940 may display only the image 941 so that it can only be seen.

Furthermore, according to another exemplary embodiment, the first display 930 may continuously display the first images 911 through 914. Furthermore, the second display 940 may display a plurality of images in the first images 911 through 914 one by one, based on an input received from the user 915 via the user input unit 320. Furthermore, the second display 940 may display at least two of the plurality of images in the first images 911 through 914 in an overlapping manner. Thus, the user is able to easily observe each of the plurality of images in the first images 911 through 914 on the second display 940.

Furthermore, the first display 930 may display the images 931 through 933 corresponding to the remaining first images 911 through 913, independently of the image 941 corresponding to the selected image 914. For example, the first display 930 may display the images 931 through 933, and the second display 940 may display the image 941. The images 931 through 933 may change over time. The image 941 may be a still image captured among the images 931 through 933 at a time point selected by the user 915. Thus, the user 915 is able to more easily observe an image taken at a specific time point on the second display 940.

Figure 9A:
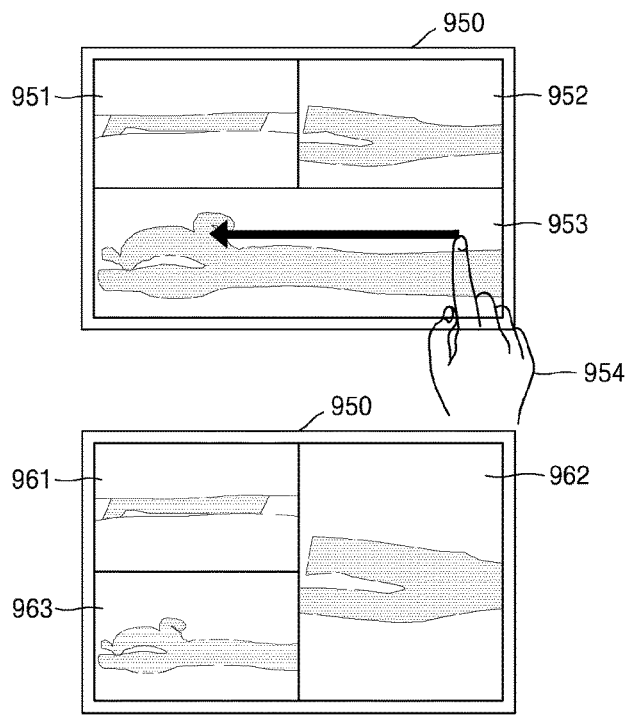
FIGS. 9A and 9B illustrate displays of an ultrasound diagnosis apparatus according to an exemplary embodiment.
Figure 9B:
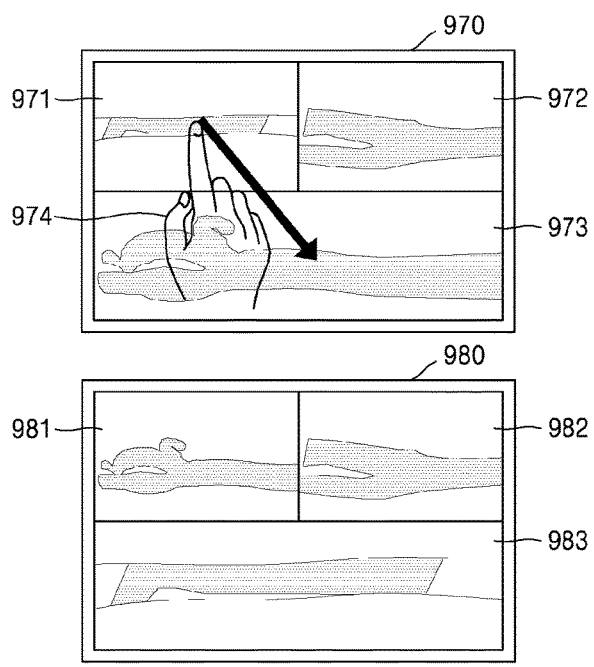

FIGS. 9A and 9B illustrate a display of the ultrasound diagnosis apparatus (300 of FIG. 3) according to an exemplary embodiment The user input unit 320 may receive a predetermined input, and the controller 340 may control at least one of a size and a position of at least one image included in images, e.g., first images 951 through 953 of FIG. 9A based on the predetermined input.

Referring to FIG. 9A, the ultrasound diagnosis apparatus 300 may include a display 950. The display 950 may be at least one of the first and second displays 311 and 312 shown in FIG. 3. The display 950 may display the first images 951 through 953 in a first image layout. For example, in the first image layout, the first images 951 through 953 may not be superimposed on one another.

The user input unit 320 may receive a predetermined input from a user 954. For example, the user input unit 320 may receive an input that occurs when the user 954 taps a right edge of the first image 953 and drags the right edge to the left. The controller 340 may reduce a size of the first image 953 based on the predetermined input. The display 950 may display a reduced version of image 963. The controller 340 may also enlarge the first image 952 and control displaying of an image 962 on a region where the first image 953 was previously displayed.

Referring to FIG. 9B, the ultrasound diagnosis apparatus 300 may include a display 970. The display 970 may be at least one of the first and second displays 311 and 312 shown in FIG. 3. The display 970 may display first images 971 through 973 in a first image layout. For example, in the first image layout, the first images 971 through 973 may not be superimposed on one another.

The user input unit 320 may receive a predetermined input from a user 974, and the controller 340 may change a position of the first image 971 based on the predetermined input. For example, if the user input unit 320 receives an input performed by tagging the first image 971 and dragging it to the lower-right direction, the controller 340 may change the position of the first image 971 to a position of the first image 973. For example, the size of the first image 971 may be changed so that it is equal to that of the first image 973, and the display 980 may display an image 983 obtained by changing the size and position of the first image 971.

Figure 10A:
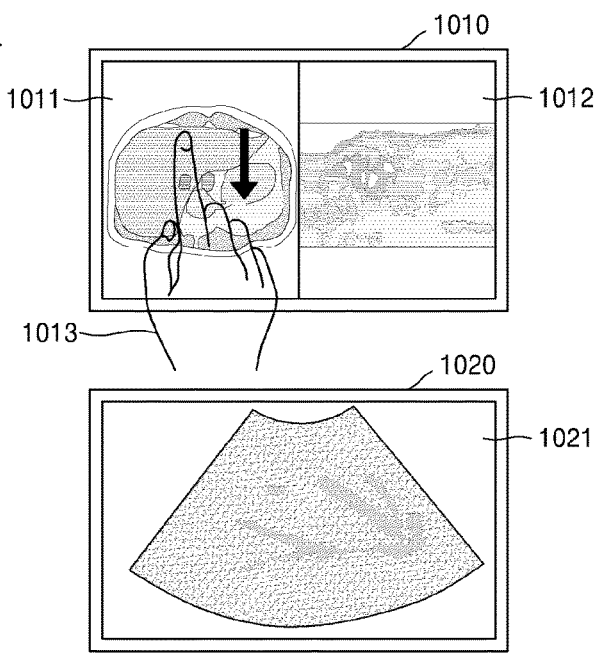
FIGS. 10A and 10B illustrate first and second displays of an ultrasound diagnosis apparatus according to an exemplary embodiment.
Figure 10B:
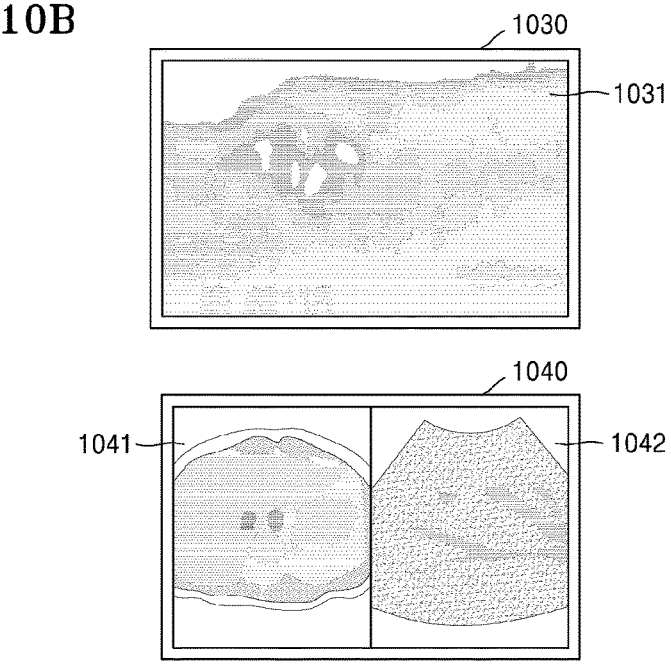

FIGS. 10A and 10B illustrate first and second displays of the ultrasound diagnosis apparatus (300 of FIG. 3) according to an exemplary embodiment.

Referring to FIG. 10A, the ultrasound diagnosis apparatus 300 may include a plurality of displays, e.g., first and second displays 1010 and 1020. The first and second displays 1010 and 1020 may respectively correspond to the first and second displays 311 and 312 shown in FIG. 3.

The first display 1010 may display a plurality of images, e.g., first images 1011 and 1012. The first images 1011 and 1012 may be displayed in a first image layout so that they are not superimposed on each other. The first images 1011 and 1012 may include at least one selected from a plurality of ultrasound images, a plurality of MRI images, and a plurality of CT images. Furthermore, the second display 1020 may display a second image 1021. For example, the second image 1020 may include at least one selected from ultrasound, MRI, and CT images.

The user input unit 320 may receive an input for selecting at least one of the first images 1011 and 1012. The input may include at least one selected from a touch input, a touch gesture input, and a button input. For example, the user input unit 320 may receive an input performed by tapping the first image 1011 and dragging it towards the second display 1020.

FIG. 10B illustrates first and second displays 1030 and 1040 after the user input unit 320 receives an input for selecting the first image 1011 from among the first images 1011 and 1012 shown in FIG. 10A.

Referring to FIG. 10B, the controller 340 may control displaying of an image 1031 corresponding to the remaining first image 1012 other than the selected first image 1011 on the first display 1030 in a fourth image layout. For example, in the fourth image layout, the image 1031 may be displayed on the entire screen of the display 1030. For example, the first display 1030 may display the image 1031 by displaying the first image 1012 shown in FIG. 10A on the entire screen. Thus, a user 1013 is able to more easily observe the image 1031 on a large screen.

The controller 340 may also control displaying of images 1041 and 1042 respectively corresponding to the selected image 1011 and the second image 1021 on the second display 1040 in a third image layout. For example, the controller 340 may divide the second display 1040 into first and second regions and control displaying of the images 1041 and 1042 on the first and second regions, respectively. Thus, the selected image 1011 and the second image 1021 may be arranged on a single screen so that they are not superimposed on each other, thereby allowing the user 1013 to easily compare the images 1041 and 1042 on the single screen.

Figure 11A:
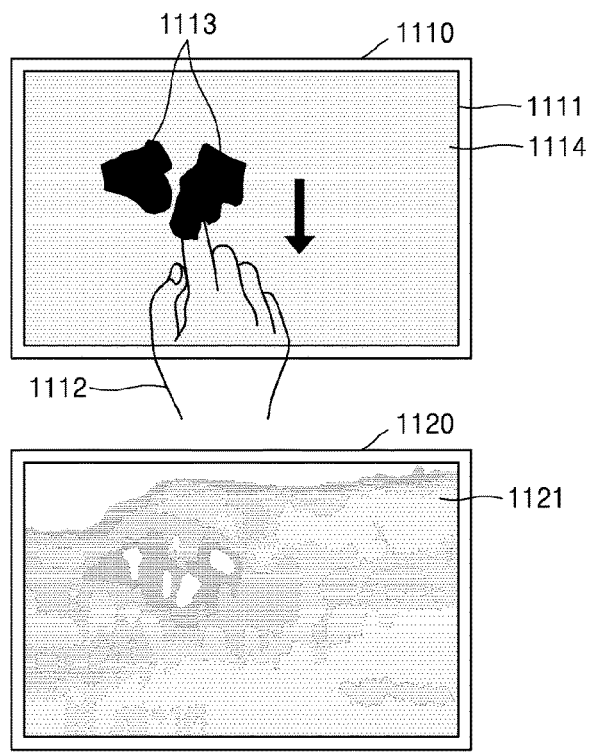
FIGS. 11A through 11F illustrate first and second displays of an ultrasound diagnosis apparatus according to an exemplary embodiment.

FIGS. 11A through 11 F illustrate first and second displays of the ultrasound diagnosis apparatus (600 of FIG. 6) according to an exemplary embodiment.

Referring to FIG. 11A, a first display 1110 may display at least one image. For example, the first display 1110 may display first images including an image 1111. For convenience of explanation, FIG. 11A illustrates an example where the first display 1110 displays only the image 1111. The first display 1110 may display a region 1113 of the image 1111 opaquely and a region 1114 thereof transparently. Furthermore, a second display 1120 may display second images including an image 1121. The first and second images may each include at least one selected from ultrasound, MRI, and CT images.

The user input unit (320 of FIG. 3) may receive an input for selecting the image 1111 from among the first images from a user 1112. The input may include at least one selected from a touch input, a touch gesture input, and a button input.

Figure 11B:
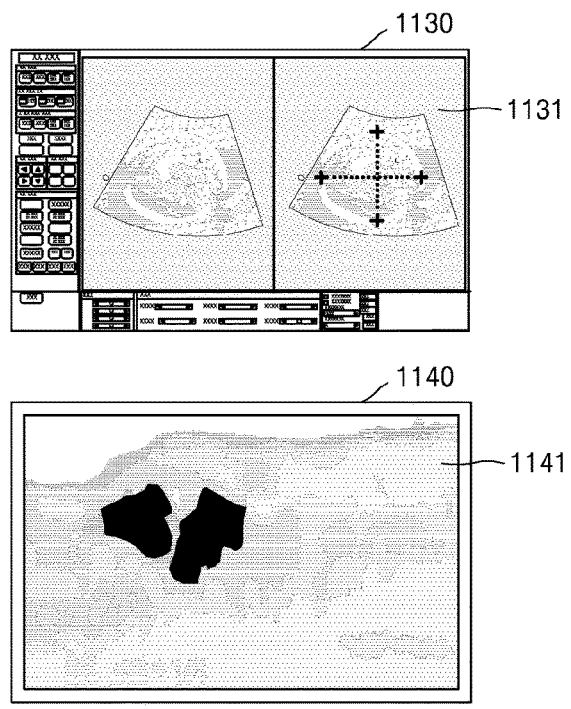

FIG. 11B illustrates first and second displays 1130 and 1140 after the user input unit 320 receives an input for selecting the image 1111 from among the first images.

Referring to FIG. 11B, the controller 340 may control displaying of an image 1141 obtained by superimposing the selected image 1111and second images on the second display 1140 in a third image layout. For example, in the third image layout, the entire image 1121 and the selected image 1111 may be superimposed on each other. The controller 340 may construct an image by placing the selected image 1111 in front of the image 1121. The image 1111 may be displayed in an opaque region thereof while the image 1121 placed behind the image 1111 may be displayed in a transparent region of the image 1111. Displaying the image 1141 including a plurality of superimposed images, e.g., the images 1111 and 1121, allows a user to more easily observe the plurality of superimposed images.

According to an exemplary embodiment, the first display 1130 may display an image 1131 indicating a menu for controlling the ultrasound diagnosis apparatus 600. In detail, referring to FIG. 11A, the first display 1110 may not display an image 1131 arranged behind the image 1111. However, referring to FIG. 11C, since the image 1111 is moved to the second display 1140, the first display 1130 may display the image 1131.

Although not shown in FIG. 11B, according to another exemplary embodiment, the first display 1130 may also continue to display the image 1111 while the second display 1140 is displaying the image 1141. For example, the second display 1140 may display the image 1141 obtained by combining the images 1111 and 1121 together. Furthermore, the first display 1130 may display first images including the image 1111. Thus, the first and second displays 1130 and 1140 may display images obtained by combining the image 1111 with different images, respectively, to thereby allow a user to view the combined images.

FIGS. 11C through 11F are diagrams for explaining a method of superimposing images according to an exemplary embodiment.

Figure 11C:
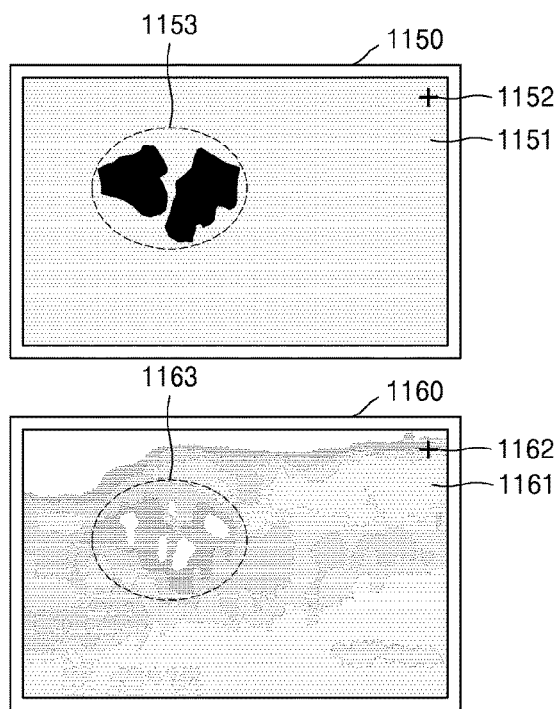

Referring to FIG. 11C, a first display 1150 may display an image 1151. The image 1151 may include at least one of a first virtual point 1152 and a first virtual region 1153. A second display 1160 may also display an image 1161, and the image 1161 may include at least one of a second virtual point 1162 and a second virtual region 1163. The first and second virtual points 1152 and 1162 and the first and second virtual regions 1153 and 1163 may be reference points and reference regions for superimposing the images 1151 and 1161 over each other, respectively.

Furthermore, the first and second virtual points 1152 and 1162 and virtual regions 1153 and 1163 may be designated by a user and automatically set via image processing by the ultrasound diagnosis apparatus 300

Figure 11D:
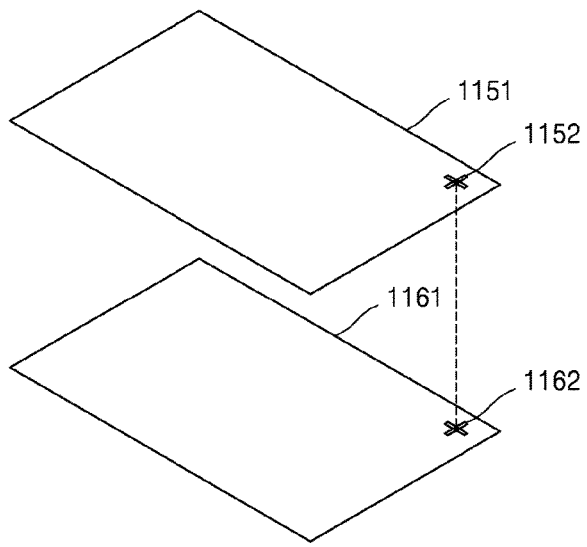

Referring to FIG. 11D, the controller 340 may superimpose the images 1151 and 1161 over each other so that the first virtual point 1152 of the image 1151 may correspond to the second virtual point 1162 of the image 1161.

Figure 11E:
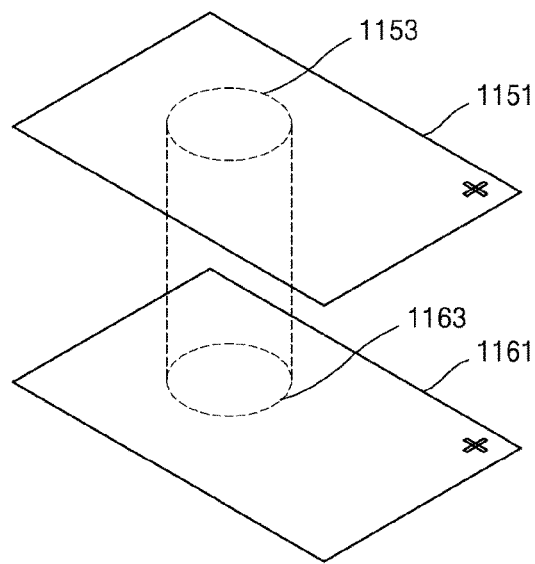

Referring to FIG. 11E, the controller 340 may superimpose the images 1151 and 1153 so that the first virtual region 1153 of the image 1151 may correspond to the second virtual region 1163 of the image 1161.

Figure 11F:
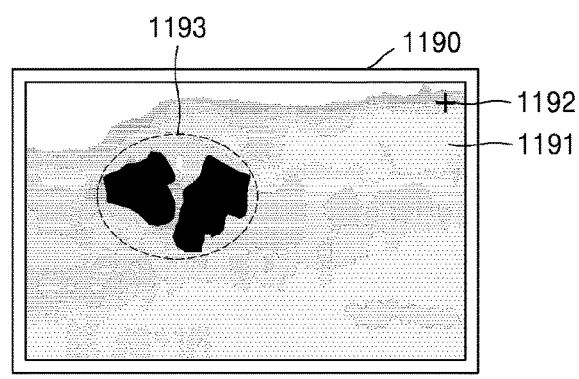

FIG. 11F illustrates a display 1190 for displaying an image obtained by superimposing images according to the method described with reference to FIGS. 11D and 11E. The display 1190 may include at least one of first and second displays 1150 and 1160. The display 1190 may display an image 1191 obtained by superimposing the images 1151 and 1161 based on the first and second virtual points 1152 and 1162 and the first and second virtual regions 1153 and 1163. The display 1190 may also display overlapping virtual points 1192 and overlapping virtual regions 1193.

Figure 12A:
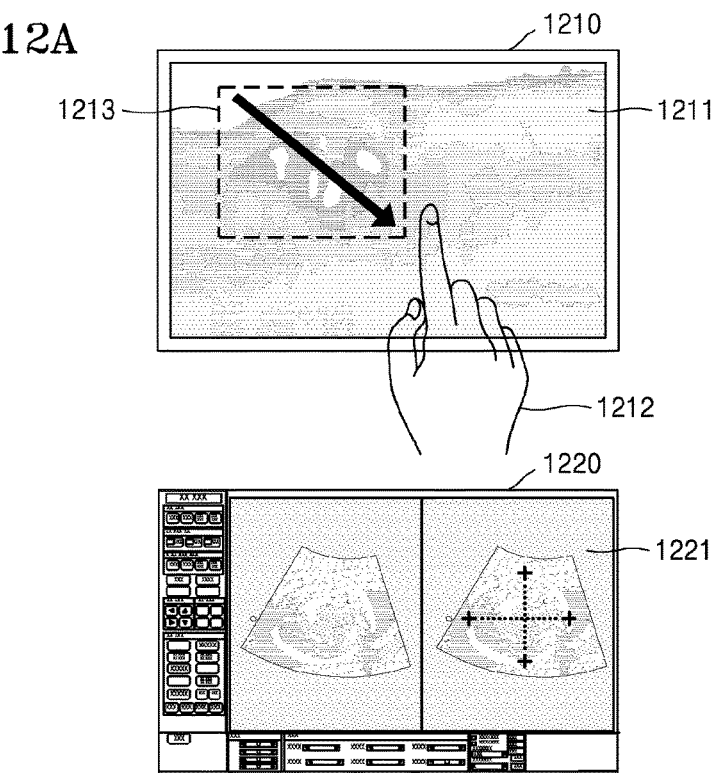
FIGS. 12A and 12B illustrate first and second displays of an ultrasound diagnosis apparatus according to an exemplary embodiment.
Figure 12B:
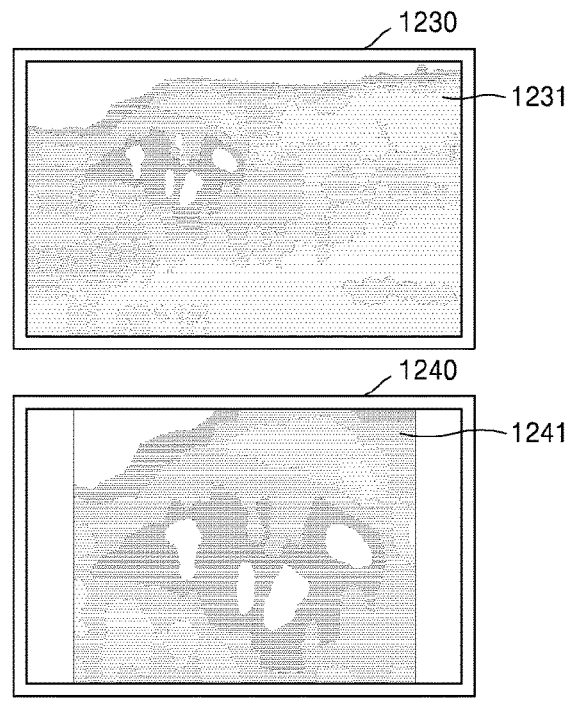

FIGS. 12A and 12B illustrate first displays 1210 and 1230 and second displays 1220 and 1240 of the ultrasound diagnosis apparatus 300 according to another exemplary embodiment.

Referring to FIG. 12A, the first display 1210 may display at least one image. For example, the first display 1210 may display first images including an image 1211. The second display 1220 may display second images including an image 1221. For convenience of explanation, FIG. 12A illustrates an example where the first and second displays 1210 and 1220 display only the images 1211 and 1221, respectively.

The user input unit 320 may receive an input for selecting a region 1213 from among the image 1211. The input may include at least one selected from a touch input, a touch gesture input, and a button input.

FIG. 12B illustrates the first and second displays 1230 and 1240 after the user input unit 320 receives the input for selecting the region 1213.

Referring to FIG. 12B, the controller 340 may control displaying of at least one selected from an image 1241 corresponding to the selected region 1213 and the second images on the second display 1240 in a third image layout. For example, in the third image layout, the image 1241 may be superimposed in front of the image 1221, so the second display 1240 may display only the image 1241. The image 1241 is obtained by enlarging the region 1213 of the image 1211. Thus, the user may observe the region 1213 more minutely by viewing the image 1241.

Figure 13A:
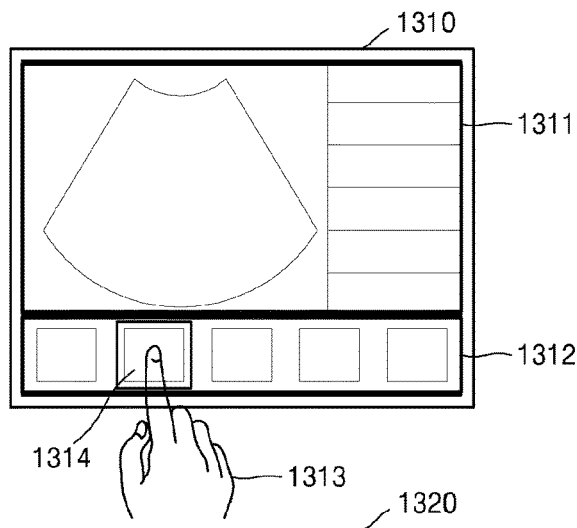
FIGS. 13A and 13B illustrate first and second displays of an ultrasound diagnosis apparatus according to an exemplary embodiment.
Figure 13A:
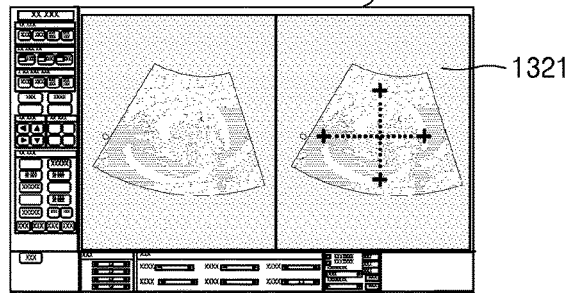
Figure 13B:
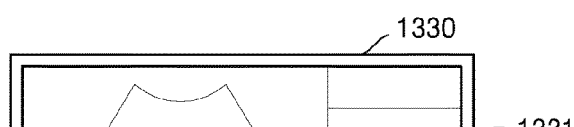
Figure 13B:
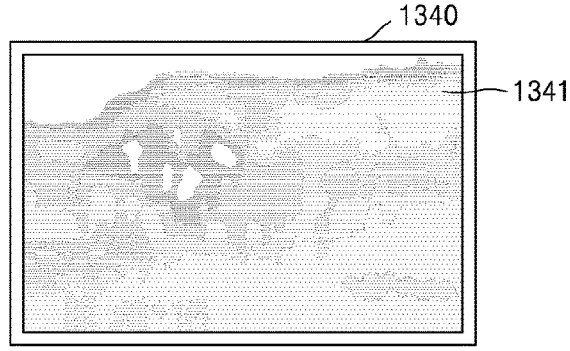

FIGS. 13A and 13B illustrate first displays 1310 and 1330 and second displays 1320 and 1340 of the ultrasound diagnosis apparatus 300 according to another exemplary embodiment Referring to FIG. 13A, the first display 1310 may display a plurality of images. For example, the first display 1310 may include a region 1311 for displaying images and a region 1312 for displaying thumbnails. A plurality of thumbnail images may be displayed on the region 1312. A larger version of at least one of the plurality of thumbnail images may also be displayed on the region 1311. Furthermore, the second display 1320 may display second images including an image 1321. For convenience of explanation, FIG. 13A illustrates an example where the second display 1320 displays only the image 1321.

The user input unit 320 may receive an input for selecting at least one 1314 of the plurality of thumbnail images displayed on the region 1312. The input may include at least one selected from a touch input, a touch gesture input, and a button input.

FIG. 13B illustrates the first and second displays 1330 and 1340 after the user input unit 320 receives the input for selecting the thumbnail image 1314.

Referring to FIG. 13B, the controller 340 may control displaying of at least one selected from an image 1341 corresponding to the selected thumbnail image 1314 and the second images on the second display 1340 in a third image layout. For example, in the third image layout, the image 1341 may be superimposed in front of the image 1321. The image 1341 is obtained by enlarging the image 1314. Thus, the user may observe the image 1314 more minutely by viewing the image 1341.

Figure 14:
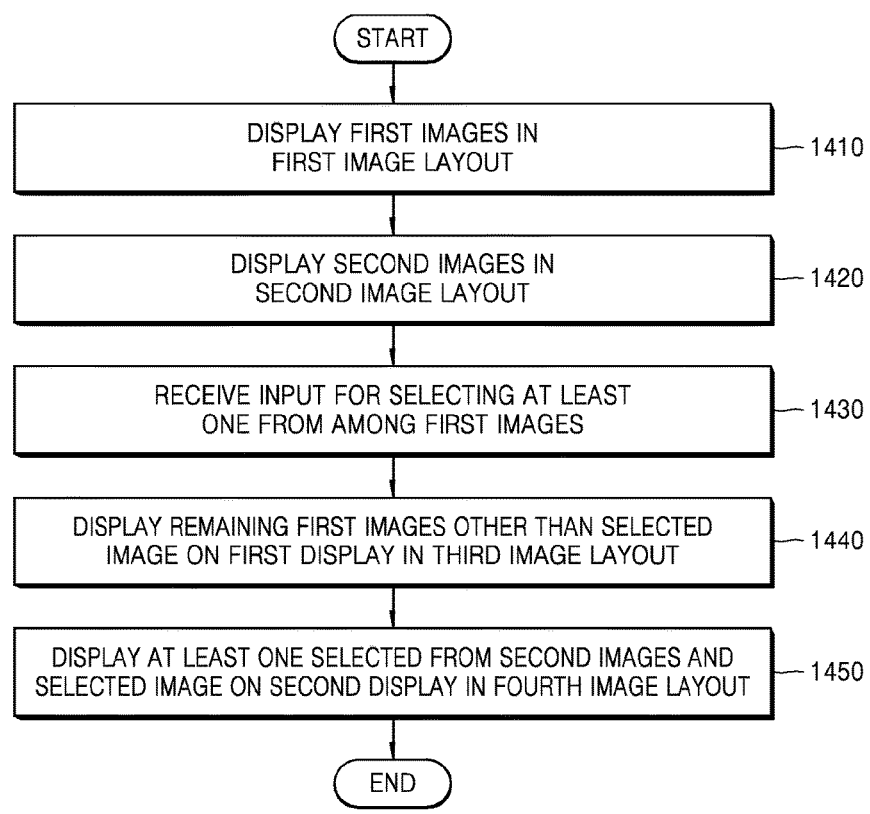
FIG. 14 is a flowchart of a method of operating an ultrasound diagnosis apparatus according to an exemplary embodiment.

FIG. 14 is a flowchart of a method of operating the ultrasound diagnosis apparatus (300 of FIG. 3) according to an exemplary embodiment.

The first display 311 may display first images in a first image layout (operation 1410). The second display 312 may display second images in a second image layout (operation 1420). The user input unit 320 may receive an input for selecting at least one from among the first images (operation 1430). The controller 340 may control displaying of at least one selected from the second images and the selected image on the second display 312 in a third image layout (operation 1440).

Furthermore, the controller 340 may control displaying of the remaining ones of the first images other than the selected image on the first display 311 in a fourth image layout (operation 1450). The controller 340 may set the fourth image layout so that the entire screen of the first display 311 is filled with the remaining first images. In the first image layout, the first images are superimposed on one another. The first images may include at least one selected from a Doppler image, a color Doppler image, an elasticity image, a photoacoustic image, an image using contrast medium, and a fusion image.

Furthermore, the controller 340 may set the third image layout so that at least some of the second images and the at least one selected image are superimposed on one another. Alternatively, the controller 340 may set the third image layout so that at least some of the second images and the selected image are not superimposed on one another.

Furthermore, the controller 340 may set the third image layout so that the entire screen of the second display 312 is filled with the second images and the selected image.

The selected image may be an image of a region of interest (ROI) selected by a user from at least one of the first images. Furthermore, the first images may be thumbnail images, and the selected image may be at least one of the thumbnail images.

The user input unit 320 may receive a predetermined input from the user. The controller 340 may control at least one of a size and a position of at least one image included in the first and second images, based on the predetermined input. An input for selecting at least one from among the first images may include at least one selected from at least one selected from a touch input, a touch gesture input, and a button input. The first and second images may each include at least one selected from MRI, CT, and ultrasound images.

The method of operating an ultrasound diagnosis apparatus according to an exemplary embodiment may be performed via a program recorded on a computer-readable recording medium.

The above method can be recorded in programs that can be executed on a computer and be implemented through general purpose digital computers which can run the programs using a computer-readable recording medium. Data structures described in the above method can also be recorded on a computer-readable medium in a variety of ways, with examples of the medium including recording media, such as magnetic storage media (e.g., Read-Only Memory (ROM), Read-Access Memory (RAM), Universal Serial Bus (USB), floppy disks, hard disks, etc.), optical recording media (e.g., Compact Disc (CD)-ROMs or Digital Versatile Discs (DVDs)), and PC interfaces (e.g., PCI, PCI-express, or Wi-Fi).

While one or more exemplary embodiments have been described with reference to the figures, it will be understood by those of ordinary skill in the art that various changes in form and details may be made therein without departing from the spirit and scope as defined by the following claims. Thus, it will be understood that the exemplary embodiments described herein should be considered in a descriptive sense only and not for purposes of limitation. The scope of the inventive concept is defined not by the detailed description thereof but by the appended claims, and all differences within the scope of the appended claims and their equivalents will be construed as being included in the inventive concept.

What is claimed is:

1. An ultrasound diagnosis apparatus comprising:
at least one memory storing instructions;
a first display configured to display first images including an ultrasound image based on divided regions of a first screen of the first display according to a first image layout;
a second display that is a different device from the first display and is configured to display second images based on divided regions of a second screen of the second display according to a second image layout; and
a controller configured to execute the stored instructions to:
receive, by the first display, an input of tapping and dragging a first medical image, among the first images, that is displayed in a first region of the first screen among the divided regions of the first screen, towards the second display,
control, in response to the input, displaying the first medical image in a first region of the second screen, reducing the second images to fit in a region other than the first region of the second screen and displaying the reduced second images in the region according to a third image layout, and
control enlarging a second medical image, among the first images, that is displayed in a second region of the first screen to fit in the first region and the second region of the first screen, and displaying the second medical image in the first region and the second region of the first screen according to a fourth image layout.

2. The ultrasound diagnosis apparatus of claim 1, wherein in the first image layout, the first images are superimposed on one another.

3. The ultrasound diagnosis apparatus of claim 2, wherein the first images comprise at least one selected from a Doppler image, a color Doppler image, an elasticity image, a photoacoustic image, an image using contrast medium, and a fusion image.

4. The ultrasound diagnosis apparatus of claim 1, wherein the controller is further configured to execute the stored instructions to set the third image layout so that at least some of the second images and the first medical image are superimposed on one another.

5. The ultrasound diagnosis apparatus of claim 1, wherein the controller is further configured to execute the stored instructions to set the third image layout so that at least some of the second images and the first medical image are not superimposed on one another.

6. The ultrasound diagnosis apparatus of claim 1, wherein the controller is further configured to execute the stored instructions to set the third image layout so that an entire screen of the second display is filled with the second images and the first medical image.

7. The ultrasound diagnosis apparatus of claim 1, wherein the first medical image is an image of a region of interest (ROI) selected by a user from at least one of the first images.

8. The ultrasound diagnosis apparatus of claim 1, wherein the first images are thumbnail images, and
wherein the first medical image is at least one of the thumbnail images.

9. The ultrasound diagnosis apparatus of claim 1, wherein the controller is further configured to execute the stored instructions to receive a predetermined input, and to control at least one of a size and a position of at least one image included in the first and second images based on the predetermined input.

10. The ultrasound diagnosis apparatus of claim 1, wherein the input for selecting the first medical image among the first images comprises at least one selected from a touch input, a touch gesture input, and a button input.

11. The ultrasound diagnosis apparatus of claim 1, wherein the second images comprise at least one selected from magnetic resonance images, computed tomography images, and ultrasound images.

12. A method of operating an ultrasound diagnosis apparatus, the method comprising:
displaying, on a first display, first images including an ultrasound image based on divided regions of a first screen of the first display according to a first image layout;
displaying, on a second display, second images, which is a different device from the first display, based on divided regions of a second screen of the second display according to a second image layout;
receiving, by the first display, an input of tapping and dragging a first medical image, among the first images, that is displayed in a first region of the first screen among the divided regions of the first screen, towards the second display;

displaying, in response to the input, the first medical image in a first region of the second screen, reducing the second images to fit in an region other than the first region of the second screen and displaying the reduced second images in the region according to a third image layout; and enlarging a second medical image, among the first images, that is displayed in a second region of the first screen to fit in the first region and the second region of the first screen, and displaying the second medical image in the first region and the second region of the first screen according to a fourth image layout.

13. The method of claim 12, wherein, in the first image layout, the first images are superimposed on one another.

14. The method of claim 13, wherein the first images comprise at least one selected from a Doppler image, a color Doppler image, an elasticity image, a photoacoustic image, an image using contrast medium, and a fusion image.

15. The method of claim 12, further comprising setting the third image layout so that at least some of the second images and the first medical image are superimposed on one another.

16. The method of claim 12, further comprising setting the third image layout so that at least some of the second images and the first medical image are not superimposed on one another.

17. The method of claim 12, further comprising setting the third image layout so that an entire screen of the second display is filled with the second images and the first medical image.

18. The method of claim 12, wherein the first medical image is an image of a region of interest (ROI) selected by a user from at least one of the first images.

19. The method of claim 12, wherein the first images are thumbnail images, and wherein the first medical image is at least one of the thumbnail images.

20. The method of claim 12, further comprising:
receiving a predetermined input; and
controlling at least one of a size and a position of at least one image included in the first and second images based on the predetermined input.

21. The method of claim 12, wherein the input for selecting the first medical image among the first images comprises at least one selected from a touch input, a touch gesture input, and a button input.

22. The method of claim 12, wherein the second images comprise at least one selected from magnetic resonance images, computed tomography images, and ultrasound images.

23. A non-transitory computer-readable recording medium having recorded thereon a program which, when executed by a computer, causes the computer to perform a method of operating an ultrasound diagnosis apparatus, the method comprising:

displaying, on a first display, first images including an ultrasound image based on divided regions of a first screen of the first display according to a first image layout;

displaying, on a second display, second images, which is a different device from the first display, based on divided regions of a second screen of the second display according to a second image layout;

receiving, by the first display, an input of tapping and dragging a first medical image, among the first images, that is displayed in a first region of the first screen among divided regions of the first screen, towards the second display;

displaying, in response to the input, the first medical image in a first region of the second screen, reducing the second images to fit in an region other than the first region of the second screen, and displaying the reduced second images in the region according to a third image layout; and enlarging a second medical image, among the first images, that is displayed in a second region of the first screen to fit in the first region and the second region of the first screen, and displaying the second medical image in the first region and the second region of the first screen according to a fourth image layout.

* * * * *